United States Patent
Bleakman et al.

(10) Patent No.: US 6,566,370 B1
(45) Date of Patent: May 20, 2003

(54) SELECTIVE IGLUR$_5$ RECEPTOR ANTAGONISTS FOR THE TREATMENT OF MIGRAINE

(75) Inventors: David Bleakman, Zionsville, IN (US); Sandra Ann Filla, Franklin, IN (US); Kirk Willis Johnson, Carmel, IN (US); Paul Leslie Ornstein, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/009,655

(22) PCT Filed: Jun. 27, 2000

(86) PCT No.: PCT/US00/16297

§ 371 (c)(1),
(2), (4) Date: Dec. 11, 2001

(87) PCT Pub. No.: WO01/01972

PCT Pub. Date: Jan. 11, 2001

Related U.S. Application Data

(60) Provisional application No. 60/142,485, filed on Jul. 6, 1999, and provisional application No. 60/151,165, filed on Aug. 27, 1999.

(51) Int. Cl.$^7$ .................. C07D 217/12; A61K 31/47
(52) U.S. Cl. ........................ 514/307; 546/147
(58) Field of Search .................. 514/307; 546/146, 546/147

(56) References Cited

U.S. PATENT DOCUMENTS

| | | | |
|---|---|---|---|
| 5,356,902 A | 10/1994 | Ornstein | 514/307 |
| 5,446,051 A | 8/1995 | Ornstein | 514/307 |
| 5,670,516 A | 9/1997 | Arnold et al. | 514/307 |
| 5,767,117 A | 6/1998 | Moskowitz | 514/307 |

FOREIGN PATENT DOCUMENTS

| | | |
|---|---|---|
| WO | WO 98/45270 | 10/1998 |
| WO | WO 01/02367 | 1/2001 |

OTHER PUBLICATIONS

Procter et al: "Possible role of GluR5 glutamate receptors in spinal nociceptive processing in the anaesthetized rat" Journal of Physiology (1997) 504.P 101P–102P.

Nikam et al: The Search for AMPA/Gly(N) receptor antagonists: Drugs of the Future 1999, 24(10): 1107–1124.

O'Neill MJ et al: "Decahydroisoquinolines: Novel competitive AMPA/kainate antagonists with neuroprotective effects in global cerebral ischaemia" Neuropharmacology 37 (1998) 1211–1222.

Proctor MJ et al: "Actions of kainite and AMPA selective glutamate receptor ligands on nociceptive processing in the spinal cord." Neuropharmacoloby 37 (1998) 1287–1297.

Bleakman D.: "Kainate receptor pharmacology and physiology" Cellular and Molecular Life Sciences 56/7–8 (1999) 558–556.

Simmons RM et al: "Kainate GluR5 receptor subtype mediates the nociceptive response to formalin in the rat" Neuropharmacology 37(1) (1998) 25–36.

National Library of Medicine (NLM), Bethesda, MD, US: Mitsilostas DD et al: "Non–NMDA glutamate receptors modulate capsaicin induced c–fos expression within trigeminal nucleus caudalis" Database accession No. 10003939 & British Journal of Pharmacology, (1999 127(3) 623–630.

Y. Sahara, et al., "Glutamate Receptor Subunits GluR5 and KA–2 Are Coexpressed in Rat Trigeminal Ganglion Neurons," *The Journal of Neuroscience*, 17(17), pp. 6611–6620 (1997).

Z. Alam, et al., "Plasma levels of neuroexcitatory amino acids in patients with migraine or tension headache," *Journal of Neurological Sciences*, 156, pp. 102–106 (1998).

*Primary Examiner*—Zinna Northington Davis
(74) *Attorney, Agent, or Firm*—Alexander Wilson

(57) ABSTRACT

The present invention provides a method of treating or preventing migraine comprising administering to a patient in need thereof an effective amount of a selective iGluR$_5$ receptor antagonist. The present invention further provides novel compounds functional as selective iGluR$_5$ receptor antagonists as well as compositions and formulations comprising said selective iGluR$_5$ receptor antagonists.

16 Claims, No Drawings

SELECTIVE IGLUR$_5$ RECEPTOR ANTAGONISTS FOR THE TREATMENT OF MIGRAINE

This is a 371 of PCT/US00/16297 filed Jun. 27, 2000, which claims priority to U.S. Provisional Application No. 60/142,485, filed Jul. 6, 1999 and U.S. Provisional Application No. 60/151,165, filed Aug. 27, 1999.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits (GluR$_1$–GluR$_4$), which can assemble to form functional ion channels. Five kainate receptors have been identified which are classified as either High Affinity (KA1 and KA2) or Low Affinity (GluR$_5$, GluR$_6$, and GluR$_7$). Bleakman et al., *Molecular Pharmacology*, 49, No.4, 581,(1996).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also to participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal.

Excitatory amino acid excitotoxicity has been implicated in the pathophysiology of numerous neurological disorders. For example, excitotoxicity has been linked with the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction. In addition, it has also been reported that excitatory amino acid excitotoxicity participates in the etiology of acute and chronic pain states including severe pain, intractable pain, neuropathic pain, and post-traumatic pain.

The use of a neuroprotective agent, such as an excitatory amino acid receptor antagonist, is believed to be useful in treating or preventing these disorders and/or reducing the amount of neurological damage associated with these disorders. Excitatory amino acid receptor antagonists may also be useful as analgesic agents.

Early theories regarding the pathophysiology of migraine have been dominated since 1938 by the work of Graham and Wolff (*Arch. Neurol. Psychiatry*, 39, 737–63 (1938)). They proposed that the cause of migraine headache is vasodilatation of extracranial vessels. This view is supported by knowledge that ergot alkaloids and sumatriptan contract cephalic vascular smooth muscle and are effective in the treatment of migraine. Sumatriptan is a hydrophilic agonist at the serotonin 5-HT-1-like receptors and does not cross the blood-brain barrier (Humphrey, et al., *Ann. NY Acad. Sci.*, 600, 587–600 (1990)). Consequently, several series of compounds said to be useful for the treatment of migraine, have been developed to optimize the 5-HT$_1$-like mediated vasoconstrictive activity of sumatriptan. However, sumatriptan's contraindications, including coronary vasospasm, hypertension, and angina are also products of its vasoconstrictive activity (MacIntyre, P. D., et al., *British Journal of Clinical Pharmacology*, 34, 541–546 (1992); Chester, A. H., et al., *Cardiovascular Research*, 24, 932–937 (1990); Conner, H. E., et al., *European Journal of Pharmacology*, 161, 91–94 (1990)).

While the vascular mechanism for migraine has gained wide acceptance, there is not total agreement as to its validity. Moskowitz, for example, has shown the occurrence of migraine headaches, independent of changes in vessel diameter (*Cephalalgia*, 12, 5–7, (1992)). It is known that the trigeminal ganglion, and its associated nerve pathways, are associated with painful sensations from the face such as headache, in particular migraine. Moskowitz proposed that unknown triggers stimulate the trigeminal ganglia which innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan, as stated, are associated with contraindications as a result of sumatriptan's attendant vasoconstrictive properties.(see supra.)

5-$HT_{1D}$ receptors have been implicated as mediating the blockade of neurogenic protein extravasation. (*Neurology*, 43(suppl. 3), S16–S20 (1993)). In addition, it has been reported that $\alpha_2$, $H_3$, m-opioid and somatostatin receptors may also be located on trigeminovascular fibers and may block neurogenic plasma extravasation (Matsubara et al., *Eur. J. Pharmacol.*, 224, 145–150 (1992)). Weinshank et al. have reported that sumatriptan and several ergot alkaloids have a high affinity for the serotonin 5-$HT_{1F}$ receptor, suggesting a role for the 5-$HT_{1F}$ receptor in migraine (WO93/14201).

European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of many different conditions, including pain and migraine headache.

Recently, it has been reported that all five members of the kainate subtype, of ionotropic glutamate receptors, are expressed on rat trigeminal ganglion neurons. In particular, high levels of $GluR_5$ and KA2 have been observed. (Sahara et al., *The Journal of Neuroscience*, 17(17), 6611 (1997)). Simmons et al. reported that the kainate $GluR_5$ receptor subtype mediates the nociceptive response to formalin in a rat model of persistent pain.(*Neuropharmacology*, 37, 25 (1998). Further, WO98/45270 previously disclosed that antagonists selective for the $iGluR_5$ receptor are useful for the treatment of pain, including; severe, chronic, intractable, and neuropathic pain. Noteworthy is the observation that kainate receptors have not previously been implicated in the etiology of migraine headache. In particular, selective $iGluR_5$ receptor antagonists have not been previously reported as being useful for the treatment of migraine.

Surprisingly, and in accordance with this invention, Applicants have discovered that selective antagonists of the $iGluR_5$ receptor subtype are efficacious in an animal model of neurogenic inflammation and, thus, could be useful for the treatment of migraine. Such antagonists could address a long felt need for a safe and effective treatment for migraine, without attending side effects. The treatment of neurological disorders is hereby furthered.

SUMMARY OF THE INVENTION

The present invention provides a method of treating or preventing migraine comprising administering to a patient in need thereof an effective amount of a selective $iGluR_5$ receptor antagonist or a pharmaceutically acceptable salt thereof. More specifically, the present invention provides a method of treating or preventing dural protein extravasation comprising administering to a patient in need thereof an effective amount of a selective $iGluR_5$ receptor antagonist.

In addition, the present invention provides a method of treating or preventing migraine comprising administering to a patient in need thereof an effective amount of a compound, or combination of compounds, which possesses the activity of a selective $iGluR_5$ receptor antagonist.

In another embodiment, the present invention provides a method of treating or preventing a neurological disorder, or neurodegenerative condition, comprising administering to a patient in need thereof an effective amount of a selective $iGluR_5$ receptor antagonist or a pharmaceutically acceptable salt thereof. Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity including tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; and acute and chronic pain states including severe pain, intractable pain, neuropathic pain, and post-traumatic pain.

In a further aspect, the present invention provides a compound of Formula I

Formula I

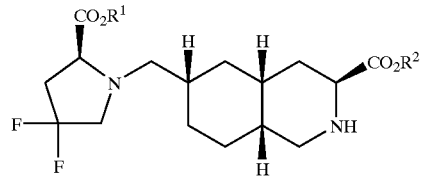

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N—$C_1$–$C_6$ dialkylamine, $C_1$–$C_6$ alkyl-pyrrolidine, $C_1$–$C_6$ alkyl-piperidine, or $C_1$–$C_6$ alkyl-morpholine; or a pharmaceutically acceptable salt thereof.

In yet another aspect, the present invention provides a method of treating or preventing migraine comprising administering to a patient in need thereof an effective amount of a compound of Formula I.

In addition, the present invention provides pharmaceutical compositions useful for treating or preventing migraine comprising selective $iGluR_5$ receptor antagonists in combination with one or more pharmaceutically acceptable carriers, diluents, or excipients.

The present invention also provides the use of a selective $iGluR_5$ receptor antagonist for the manufacture of a medicament for treating or preventing migraine.

DETAILED DESCRIPTION OF THE INVENTION

The present invention provides a method for the treatment of migraine which can be demonstrated by a particular mechanism of action, inhibition of neurogenic dural protein extravasation. By treating a migraineur with a compound or composition which is a selective antagonist of the $iGluR_5$ receptor relative to other excitatory amino acid receptors, the neurogenic extravasation which mediates migraine is inhibited without the attending side effects of agents designed to optimize the 5-$HT_1$-like mediated vasoconstrictive activity of sumatriptan. In addition, the present invention provides compounds functional as selective $iGluR_5$ receptor antagonists as well as pharmaceutically acceptable salts, prodrugs, and compositions thereof.

The term "pharmaceutically acceptable salt" as used herein, refers to salts of the compounds provided by, or employed in the present invention which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

It will be understood by the skilled reader that most or all of the compounds used in the present invention are capable of forming salts, and that the salt forms of pharmaceuticals are commonly used, often because they are more readily crystallized and purified than are the free bases. In all cases, the use of the pharmaceuticals described herein as salts is contemplated in the description herein, and often is preferred, and the pharmaceutically acceptable salts of all of the compounds are included in the names of them.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981.

The compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of Formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization. and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

It should also be understood by the skilled artisan that all of the compounds useful for the methods of the present invention are available for prodrug formualtion. "Prodrug" as used herein, refers to metabolically labile ester or diester derivative of the functional acid compounds(drugs) provided by, or employed in the methods of, the present invention. When administered to a patient, the prodrug undergoes enzymatic and/or chemical hydrolytic cleavage in such a manner that the parent carboxylic acid (drug), or as the case may be the parent dicarboxylic acid, is released. In all cases, the use of the compounds described herein as prodrugs is contemplated, and often is preferred, and thus, the prodrugs of all of the compounds employed are encompassed in the names of the compounds herein.

As used herein the term "$C_1$–$C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1$–$C_6$ alkyl" refers to a straight or branched, monovalent, saturated aliphatic chain of I to 6 carbon atoms and includes, but is not limited to methyl, ethyl, n-propyl, isopropyl, n-butyl, isobutyl, t-butyl, n-pentyl, n-hexyl, and the like.

As used herein the term "$C_1$–$C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$C_1$–$C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein, the terms "Me", "Et", "Pr", "iPr", "Bu" and "t-Bu" refer to methyl, ethyl, propyl, isopropyl, butyl and tert-butyl respectively.

As used herein the term "$C_2$–$C_6$ alkenyl" refers to a straight or branched, monovalent, unsaturated aliphatic chain having from two to six carbon atoms. Typical $C_2$–$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

As used herein, the term "$C_1$–$C_6$ alkylaryl" refers to a straight or branched, monovalent, saturated aliphatic chain of 1 to 6 carbon atoms which has an aryl group attached to the aliphatic chain. Included within the term "$C_1$–$C_6$ alkylaryl" are the following:

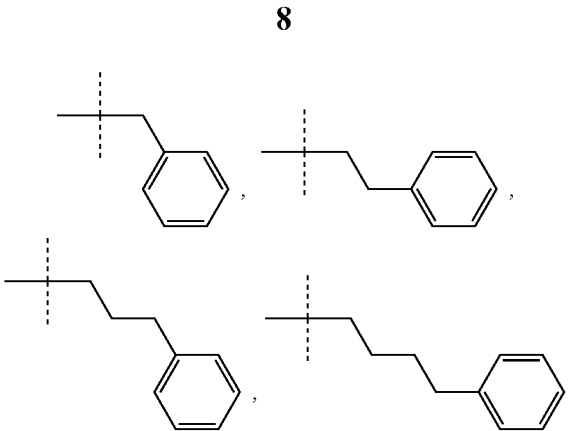

and the like.

As used herein the term "$(C_3$–$C_{10})$cycloalkyl" refers to a saturated hydrocarbon ring structure containing from three to ten carbon atoms. Typical $C_3$–$C_{10}$ cycloalkyl groups include cyclopropyl, cyclobutyl, cyclopentyl, cyclohexyl, cycloheptyl, cyclooctyl, and the like. It is understood that "$(C_3$–$C_8)$cycloalkyl" and "$(C_4$–$C_6)$cycloalkyl" is included within the term "$(C_3$–$C_{10})$cycloalkyl".

As used herein, the term "$C_1$–$C_6$ alkyl($C_3$–$C_{10}$)cycloalkyl" refers to a straight or branched, monovalent, saturated aliphatic chain of 1 to 6 carbon atoms which has a ($C_3$–$C_{10}$)cycloalkyl attached to the aliphatic chain. Included within the term "$C_1$–$C_6$ alkyl($C_3$–$C_{10}$)cycloalkyl" are the following:

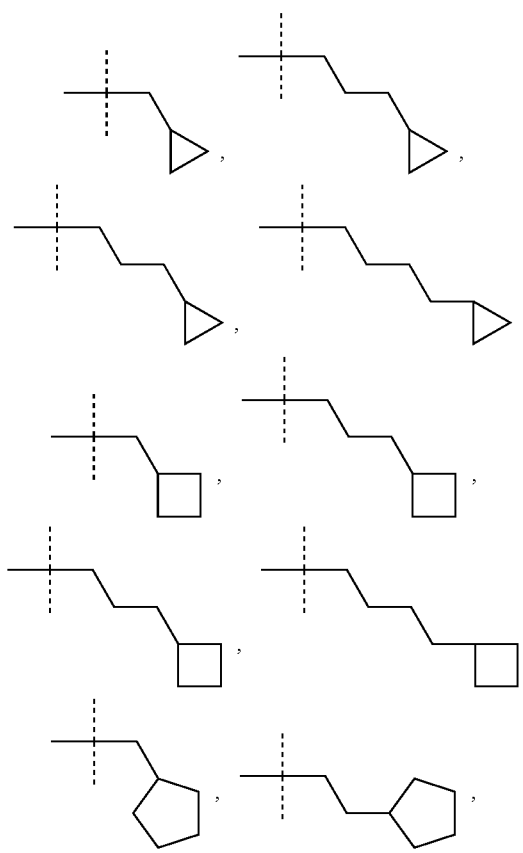

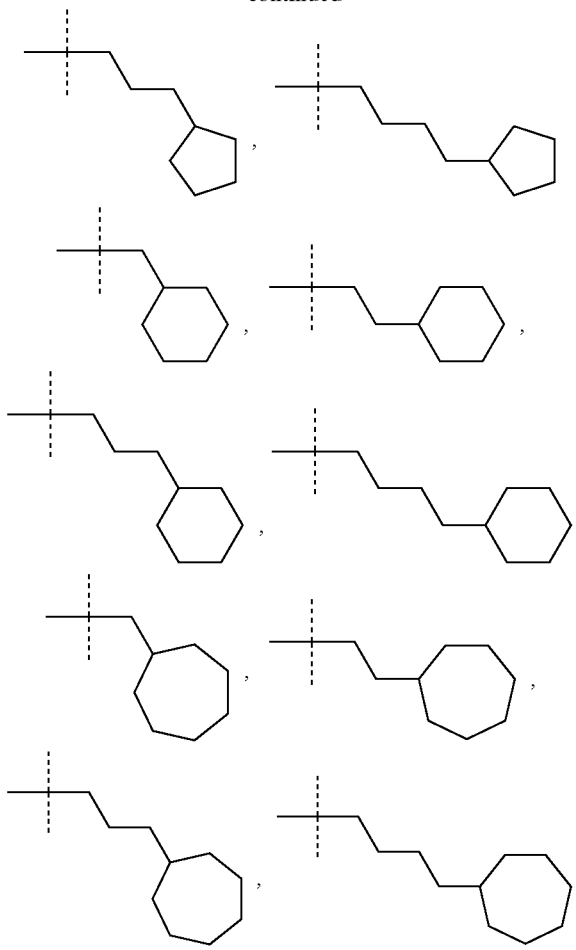

and the like.

As used herein the term "N,N—C$_1$–C$_6$ dialkylamine" refers to a nitrogen atom substituted with two straight or branched, monovalent, saturated aliphatic chains of 1 to 6 carbon atoms. Included within the term "N,N-C$_1$–C$_6$ dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "C$_1$–C$_6$ alkyl-N,N-C$_1$–C$_6$ dialkylamine" refers to straight or branched, monovalent, saturated aliphatic chain of 1 to 6 carbon atoms which has an N,N-C$_1$–C$_6$ dialkylamine attached to the aliphatic chain. Included within the term "C$_1$–C$_6$ alkyl-N,N-C$_1$–C$_6$ dialkylamine" are the following:

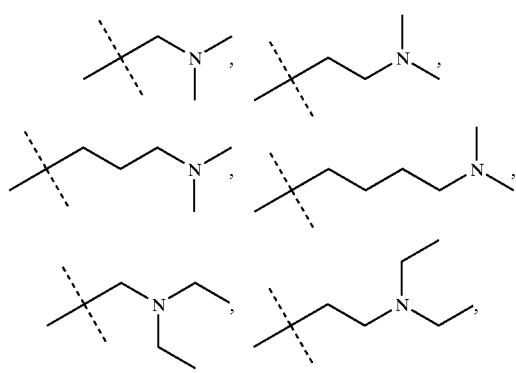

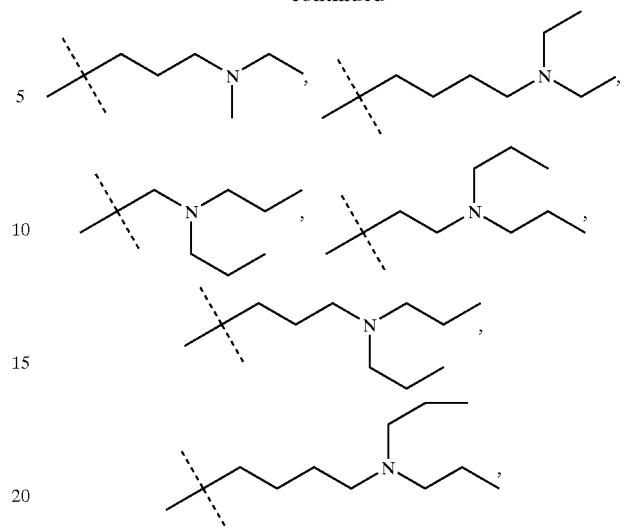

and the like.

As used herein the term "C$_1$–C$_6$ alkyl-pyrrolidine" refers to a straight or branched, monovalent, saturated aliphatic chain of 1 to 6 carbon atoms which has a pyrrolidine attached to the aliphatic chain. Included within the scope of the term "C$_1$–C$_6$ alkyl-pyrrolidine" are the following:

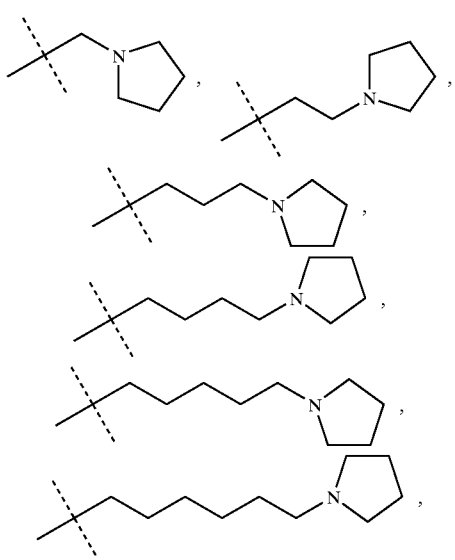

and the like.

As used herein the term "C$_1$–C$_6$ alkyl-piperidine" refers to a straight or branched, monovalent, saturated aliphatic chain of 1 to 6 carbon atoms which has a piperidine attached to the aliphatic chain. Included within the scope of the term "C$_1$–C$_6$ alkyl-piperidine" are the following:

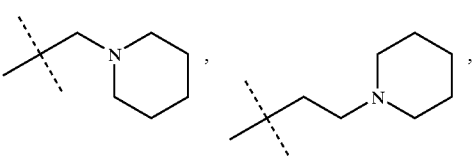

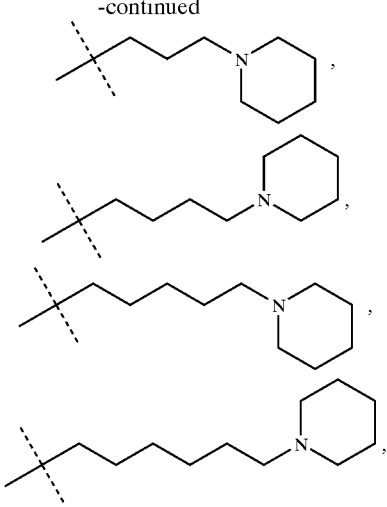

and the like.

As used herein the term "$C_1$–$C_6$ alkyl-morpholine" refers to a straight or branched, monovalent, saturated aliphatic chain of 1 to 6 carbon atoms which has a morpholine attached to the aliphatic chain. Included within the scope of the term "$C_1$–$C_6$ alkyl-morpholine" are the following:

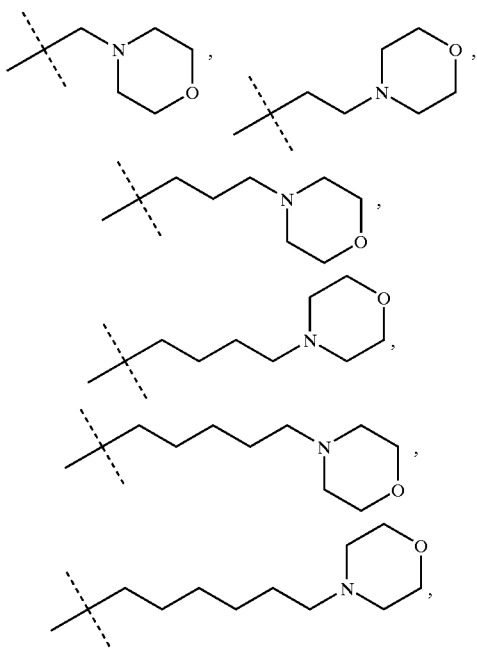

and the like.

The designation "◀━" refers to a bond that protrudes forward out of the plane of the page.

The designation "⋯⋯" refers to a bond that protrudes backward out of the plane of the page.

As used herein the term "$iGluR_5$" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormality such as those resulting from tumor or stroke), gasrointestinal disturbances, and possibly neurological symptoms such as visual distortion. Characteristic headaches of migraine usually last one day and are commonly accompanied by nausea, emesis, and photophobia.

Migraine is a "chronic" condition. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human.

It is understood that the term "selective $iGluR_5$ receptor antagonist" as used herein, includes those excitatory amino acid receptor antagonists which selectively bind to the $iGluR_5$ kainate receptor subtype, relative to the $iGluR_2$ AMPA receptor subtype. Preferably the selective $iGluR_5$ antagonist for use according to the method of the present invention has a binding affinity at least 10 fold greater for $iGluR_5$ than for $iGluR_2$, more preferably at least 100 fold greater. It is further understood that any selective $iGluR_5$ antagonist, as appreciated by one of ordinary skill in the art, is included within the scope of the methods of the present invention. Such selective $iGluR_5$ receptor antagonists are readily available to, or are readily prepared by, one of ordinary skill in the art following recognized procedures. Examples of selective $iGluR_5$ receptor antagonists include, but are not limited to, the compounds provided in WO 98/45270, the entire contents of which is herein incorporated by reference.

It is further understood that the selective $iGluR_5$ receptor antagonists may exist as pharmaceutically acceptable salts and, as such, salts are therefore included within the scope of the present invention.

As used herein, the terms "treating" or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the migraine involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

The selective $iGluR_5$ antagonists for use according to the methods of the present invention may be a single compound or a combination of compounds capable of functioning as a selective $iGluR_5$ receptor antagonist. For example, it may be a combination of a compound capable of functioning as an antagonist at the $iGluR_5$ receptor and one or more other glutamate receptors, in combination with one or more compounds capable of blocking its actions at the $iGluR_2$ receptor. It is understood, however, that the selective $iGluR_5$ antagonist for use in the methods of the present invention, is preferably a single compound.

Oral administration is a preferred route of administering the compounds employed in the present invention whether administered alone, or as a combination of compounds capable of acting as a selective $iGluR_5$ receptor antagonist. Oral administration, however, is not the only route, nor even the only preferred route. Other preferred routes of administration include transdermal, percutaneous, intravenous, intramuscular, intranasal, buccal, or intrarectal routes. Where the selective $iGluR_5$ receptor antagonist is administered as a combination of compounds, one of the compounds may be administered by one route, such as oral, and the other may be administered by the transdermal, percutaneous, intravenous, intramuscular, intranasal, buccal, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating said compounds are important embodiments of the present invention. Such compositions may take any physical form which is pharmaceutically acceptable, but orally administered pharmaceutical compositions are particularly preferred. Such pharmaceutical compositions contain an effective amount of a selective $iGluR_5$ receptor antagonist, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| | |
|---|---|
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |

-continued

Formulation 7
Suspensions each containing 50 mg of medicament per
5 ml dose are made as follows:

| Color | q.v. |
|---|---|
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| Active Ingredient | 100 mg |
|---|---|
| Mannitol | 100 mg |
| 5 N Sodium hydroxide | 200 ml |
| Purified water to total | 5 ml |

It is understood by one of ordinary skill in the art that the above procedures can also be applied to a method of treating migraine comprising administering to a patient an effective amount of a compound which possesses the activity of a selective iGluR$_5$ receptor antagonist.

Inhibition of neuronal protein dural extravasation is an exemplary mechanism of action for the method of the present invention. The method further requires that compounds which exhibit such inhibition, also demonstrate selective binding and inhibition of the iGluR$_5$ receptor. The panel of compounds used to illustrate the principle of the present invention, and the pharmacological assays employed to demonstrate the mechanistic effectiveness of the invention, are described below. It is believed that Compounds III, IV(a), and IV(b) herein, represent novel compounds and, as such, have not previously been described as selective iGluR$_5$ receptor antagonists, nor reported as efficacious in treating migraine. Compounds III, IV(a), and IV(b) therefore, are provided as additional embodiments of the present invention.

The following examples illustrate the methods of the present invention. The reagents and starting materials are readily available to one of ordinary skill in the art. These examples are intended to be illustrative only and are not to be construed so as to limit the scope of the invention in any way. As used herein, the following terms have the meanings indicated: "i.v." refers to intravenously; "p.o." refers to orally; "i.p." refers to intraperitoneally; "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "mm Hg" refers to millimeters of mercury; "min" refers to minutes; "h" or "hr" refers to hours; "° C." refers to degrees Celsius; "TLC" refers to thin layer chromatography; "HPLC" refers to high performance liquid chromatography; "R$_f$" refers to retention factor; "R$_t$" refers to retention time; "δ" refers to part per million down-field from tetramethylsilane; "THF" refers to tetrahydrofuran; "DMF" refers to N,N-dimethylformamide; "DMSO" refers to dimethyl sulfoxide; "aq" refers to aqueous; "EtOAc" refers to ethyl acetate; "iPrOAc" refers to isopropyl acetate; "MeOH" refers to methanol; "MTBE" refers to tert-butyl methyl ether; "RT" refers to room temperature; "K$_i$" refers to the dissociation constant of an enzyme-antagonist complex and serves as an index of ligand binding; and "ID$_{50}$" and "ID$_{100}$" refer to doses of an administered therapeutic agent which produce, respectively, a 50% and 100% reduction in a physiological response.

EXAMPLE 1

Compound I
3S, 4aR, 6S, 8aR-6-(((4-carboxy) phenyl) methyl)-1, 2, 3, 4a, 5, 6, 7, 8, 8a decahydroisoquinoline-3-carboxylic acid

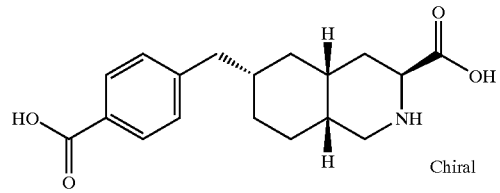

Those skilled in the art will recognize Compound I as an excitatory amino acid receptor antagonist, selective for the iGluR$_5$ receptor subtype. Compound I may be readily prepared by one of ordinary skill in the art following recognized general procedures as described in U.S. Pat. No. 5,446,051, and more specifically as recently published in international application WO 98/45270, published Oct. 15, 1998.

Compound II
3S, 4aR, 6S, 8aR-6-((((1H-Tetrazole-5-yl) methyl) oxy) methyl)-1, 2, 3, 4a, 5, 6, 7, 8, 8a-decahydroisoquinoline-3-carboxylic acid

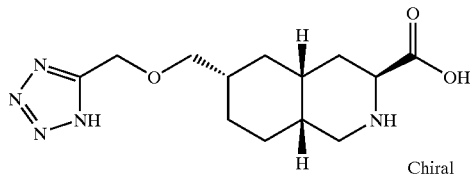

Those skilled in the art will recognize Compound II as an excitatory amino acid receptor antagonist, selective for the iGluR$_5$ receptor subtype. Compound II may be readily prepared and resolved by one of ordinary skill in the art following recognized general procedures as described in U.S. Pat. No. 5,670,516 (see Example No. 11, Compound No. 7), and more specifically as recently published in international application WO 98/45270, published Oct. 15, 1998.

Compound III

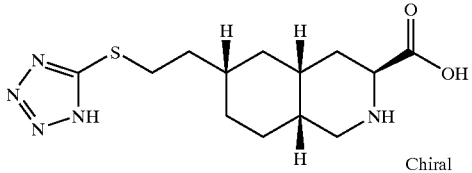

Compound III represents a novel compound, functional as a selective iGluR$_5$ receptor antagonist. Compound III may be readily prepared; the desired enantiomer may be optically resolved; and pharmaceutical compositions comprising Compound III may be readily formulated by following general methods essentially as described for Example No. 8, Compound No. 8 of U.S. Pat. No. 5,670,516, the entire contents of which is herein incorporated by reference.

Compound IV(b)

3S, 4aR, 6S, 8aR Ethyl 6-(((2S)-2-(Ethoxycarbonyl)-4,4-difluoropyrrolidinyl)methyl)-1, 2, 3, 4, 4a, 5, 6, 7, 8, 8a-decahydroisoquinoline-3-carboxylate

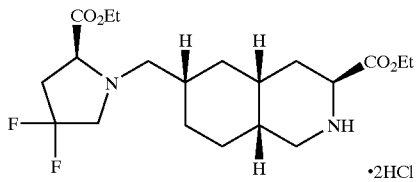

A. Preparation of 3S, 4aR, 6S, 8aR Ethyl 6-((4-Methylphenyl)sulfonyloxy)methyl)-2-methoxycarbonyl-1, 2, 3, 4, 4a, 5, 6, 7, 8, 8a-decahydroisoquinoline-3-carboxylate To a solution of 15.0 g (50.1 mmol) of hydroxymethyl intermediate (See Col.11–12, Scheme II of U.S. Pat. No. 5,356,902, the entire contents of which are herein incorporated by reference) cooled to 0° C. in $CH_2Cl_2$ (100 mL), was added triethylamine (20.9 mL, 150.3 mmol) followed by toluenesolfonyl chloride (19.1 g, 100.2 mmol) dissolved in $CH_2Cl_2$ (100 mL). The reaction was warmed to room temperature and stirred 16 h, then partitioned between $CH_2Cl_2$ and 10% aqueous $NaHSO_4$. The aqueous layer was extracted with $CH_2Cl_2$ and the combined organics were dried over $MgSO_4$, filtered, and concentrated in vacuo. Column chromatography (10–50% EtOAc/hexane) provided 20.1 g (89%) of the desired intermediate title compound as a colorless oil:

MS(m/e): 451.5 ($M^+$)

Calculated for $C_{22}H_{31}NO_7S$ 0.1 $CH_2Cl_2$: Theory: C, 57.45; H, 6.81; N, 3.03. Found: C, 57.76; H, 6.93; N, 3.35.

$^{13}C$ NMR (DMSO-$d_6$): δ 171.4, 144.8, 132.4, 130.1, 127.6, 74.6, 60.4, 53.1, 52.4, 44.1, 34.6, 31.8, 31.0, 29.8, 28.8, 24.9, 23.3, 21.0, 14.0.

B. Preparation of 3S, 4aR, 6S, 8aR Ethyl 6-(((3S, 5S)-5-(Ethoxycarbonyl)-3-hydroxypyrrolidinyl)methyl)-2-methoxycarbonyl-1, 2, 3, 4, 4a, 5, 6, 7, 8, 8a-decahydroisoquinoline-3-carboxylate A mixture of trans 4-hydroxy-L-proline ethyl ester (6.5 g, 33.1 mmol), the compound of Step A above (10.0 g, 22.0 mmol), and potassium carbonate (4.6 g, 33.1 mmol) were heated at reflux in acetonitrile (22 mL) for 60 h. The reaction mixture was cooled to room temperature, and partitioned between $CH_2Cl_2$ and water. The aqueous layer was extracted two times with $CH_2Cl_2$ and the combined organics were dried over $MgSO_4$, filtered, and concentrated in vacuo. Column chromatography (50% EtOAc/hexane followed by 5% $MeOH/CH_2Cl_2$) gave 9.2 g (95%) of the desired intermediate title compound as a colorless oil:

MS(m/e): 441.3 ($M^+$)

Calculated for $C_{22}H_{36}N_2O_7S$: Theory: C, 59.98; H, 8.24; N, 6.36. Found: C, 60.17; H, 8.23; N, 6.42.

C. Preparation of 3S, 4aR, 6S, 8aR Ethyl 6-(((5S)-5-(Ethoxycarbonyl)-3-oxopyrrolidinyl)methyl)-2-methoxycarbonyl-1, 2, 3, 4, 4a, 5, 6, 7, 8, 8a-decahydroisoquinoline-3-carboxylate.

To a solution of DMSO (2.3 mL, 32.5 mmol) cooled to −78 ° C. in $CH_2Cl_2$ (25 mL) was added, dropwise, oxalyl chloride (1.4 mL, 16.3 mmol). The reaction mixture was stirred for 5 min, then the compound of Step B above (6.0 g, 13.6 mmol) dissolved in 20 mL of $CH_2Cl_2$ was added. Upon stirring for 45 min at −78 ° C., triethylamine (9.5 mL, 32.5 mmol) was added. The reaction was warmed to room temperature over approximately 2 hours, and quenched by the addition of 10% aqueous $NaHSO_4$. The aqueous layer was extracted with $CH_2Cl_2$ and the combined organics were dried over $MgSO_4$, filtered, and concentrated in vacuo. Column chromatography (25-50% EtOAc/hexane) provided 4.6 g (78%) of the desired intermediate title compound as a colorless oil:

MS(m/e): 439.1 ($M^+$).

D. Preparation of 3S, 4aR, 6S, 8aR Ethyl 6-(((2S)-2-(Ethoxycarbonyl)-4,4-difluoropyrrolidinyl)methyl)-2-methoxycarbonyl-1, 2, 3, 4, 4a, 5, 6, 7, 8, 8a-decahydroisoquinoline-3-carboxylate.

To a mixture of the compound of Step C above (4.62 g, 10.5 mmol) cooled to −78 ° C. in $CH_2Cl_2$ (50 mL) was added, dropwise, diethylaminosulfur trifluoride (3.5 mL, 26.3 mmol). The reaction was allowed to warm to room temperature, stirred an additional 48 h, then quenched by the addition of MeOH. After concentrating in vacuo, the residue was partitioned between $CH_2Cl_2$ and saturated aqueous $NaHCO_3$. The aqueous layer was extracted with $CH_2Cl_2$ and the combined organics were dried over $MgSO_4$, filtered, and concentrated in vacuo. Column chromatography (25–50% EtOAc/hexane) provided 3.3 g (68%) of the desired intermediate title compound as a colorless oil:

MS(m/e): 461.2 ($M^+$)

Calculated for $C_{22}H_{34}F_2N_2O_6$: Theory: C, 57.38; H, 7.44; N, 6.08. Found: C, 57.28; H, 7.52; N, 6.13.

E. Preparation of 3S, 4aR, 6S, 8aR Ethyl 6-(((2S)-2-(Ethoxycarbonyl)4,4-difluoropyrrolidinyl)methyl)-1, 2, 3, 4, 4a, 5, 6, 7, 8, 8a-decahydroisoquinoline-3-carboxylate (Compound IV(b)).

A solution of the compound of Step D above (3.3 g, 7.10 mmol) dissolved in $CH_2Cl_2$ (40 mL) was cooled to 0 ° C. and charged with trimethylsilyl iodide (3.0 mL, 21.3 mmol). The reaction was allowed to warm to room temperature, stirred an additional 4 h, then quenched by the addition of saturated aqueous $NaHCO_3$ (50 mL). The aqueous layer was extracted with $CH_2Cl_2$ and the combined organics washed with a 1N solution of sodium thiosulfate, dried over $MgSO_4$, filtered, and concentrated in vacuo. The material was chromatographed, (2% $MeOH/CH_2Cl_2$), dissolved in 20 mL of $Et_2O$, and to it was added 50 mL of a $HCl/Et_2O$ solution. The solvent was removed in vacuo, providing 2.6 g (76%) of the final title compound as a white solid:

MS(m/e): 403.4 ($M^+$)

Calculated for $C_{20}H_{32}Cl_2F_2N_2O_4$: Theory: C, 50.53; H, 7.21; N, 5.89. Found: C, 50.90; H, 7.41; N, 5.84.

$^{13}C$ NMR ($D_2O$): δ 170.3, 167.7, 125.1 (t, $J_{C-F}$=249.1 Hz), 65.9, 65.0, 64.1, 63.4, 60.1 (t, $J_{C-F}$=33.9 Hz), 57.6, 52.8, 42.9, 37.2 (t, $J_{C-F}$=26.4 Hz), 34.5, 31.7, 31.3, 30.5, 28.4, 26.9, 24.3, 13.6.

Compound IV(a)

3S, 4aR, 6S, 8aR 6-(((2S)-2-(Carboxylic acid)4,4-difluoropyrrolidinyl)methyl)-1, 2, 3, 4, 4a, 5, 6, 7, 8, 8a-decahydroisoquinoline-3-carboxylic Acid

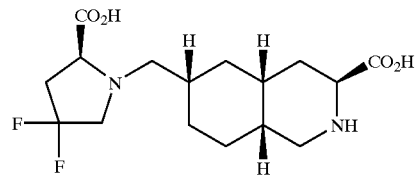

A solution of 3S, 4aR, 6S, 8aR Ethyl 6-(((2S)-2-(Ethoxycarbonyl)4,4-difluoropyrrolidinyl)methyl)-2-methoxycarbonyl-1, 2, 3, 4, 4a, 5, 6, 7, 8, 8a-decahydroisoquinoline-3-carboxylate (3.3 g, 7.10 mmol), the compound of Step D above, dissolved in 5 N aqueous HCl (15 mL) was heated at 90 ° C. for 18 h. The reaction mixture was cooled to room temperature and concentrated in vacuo. The resulting crude foam was dissolved in water (75 mL) and stirred in the presence of Dowex 50X8 (100–200) ion-exchange resin (10 g) for 2 h. The resin was filtered, washed sequentially with 1:1 THF/H$_2$O and water, then stirred in the presence of 10% pyridine/H$_2$O for 2 h. After filtration, the resin was washed with water, and the filtrate was concentrated in vacuo to provide the title compound (0.6 g, 97%) as a white foam:

MS(m/e): 347.2 (M$^+$)

Calculated for $C_{16}H_{24}F_2N_2O_4$ 0.1 H$_2$O: Theory: C, 55.19; H, 7.01; N, 8.05. Found: C, 54.81; H, 6.82; N, 8.13.

$^{13}$C NMR (D$_2$O): δ 175.1, 171.1, 125.6 (t, $J_{C-F}$=249.4 Hz), 67.9, 63.0, 59.3 (t, $J_{C-F}$=34.0 Hz), 54.5, 42.5, 37.5 (t, $J_{C-F}$=24.9 Hz), 34.3, 32.7, 32.4, 30.6, 28.2, 27.0, 24.3.

EXAMPLE 2

To establish that the iGluR$_5$ receptor subtype is mediating neurogenic protein extravasation, a functional characteristic of migraine, the binding affinity of the panel compounds to the iGluR$_5$ receptor is first measured using standard methods. For example, the activity of compounds acting at the iGluR$_5$ receptor antagonists can be determined by radiolabelled ligand binding studies at the cloned and expressed human iGluR$_5$ receptor (Korczak et al., 1994, Recept. Channels 3; 41–49), and by whole cell voltage clamp electrophysiological recordings of currents in acutely isolated rat dorsal root ganglion neurons (Bleakman et al., 1996, Mol. Pharmacol. 49; 581–585). The selectivity of compounds acting at the iGluR$_5$ receptor subtype can then be determined by comparing antagonist activity at the iGluR$_5$ receptor with antagonist activity at other AMPA and kainate receptors. Methods useful for such comparison studies include: receptor-ligand binding studies and whole-cell voltage clamp electrophysiological recordings of functional activity at human GluR$_1$, GluR$_2$, GluR$_3$ and GluR$_4$ receptors (Fletcher et al., 1995, Recept. Channels 3; 21–31); receptor-ligand binding studies and whole-cell voltage clamp electrophysiological recordings of functional activity at human GluR$_6$ receptors (Hoo et al., Recept. Channels 2;327–338); and whole-cell voltage clamp electrophysiological recordings of functional activity at AMPA receptors in acutely isolated cerebellar Purkinje neurons (Bleakman et al., 1996, Mol. Pharmacol. 49; 581–585) and other tissues expressing AMPA receptors (Fletcher and Lodge, 1996, Pharmacol. Ther. 70; 65–89).

iGluR$_5$ Antagonist Binding Affinity Profiles

Cell lines (HEK293 cells) stably transfected with human iGluR receptors were employed. Displacement of $^3$[H] AMPA by increasing concentrations of antagonist was measured on iGluR$_1$, iGluR$_2$, iGluR$_3$, and iGluR$_4$ expressing cells, while displacement of $^3$[H] kainate (KA) was measured on iGluR$_5$, iGluR$_6$, iGluR$_7$, and KA2-expressing cells. Estimated antagonist binding activity ($K_i$) in μM was determined for Compounds I–IV. As an indicia of selectivity, the ratio of binding affinity to the iGluR$_2$ AMPA receptor subtype, versus the binding affinity to iGluR$_5$ kainate receptor subtype, was also determined. Compounds provided by the present invention displayed a binding affinity of at least 10 fold greater for iGluR$_5$ than that for iGluR$_2$, more preferably at least 100 fold.

EXAMPLE 3

The following animal model was employed to determine the ability of each of the panel of compounds to inhibit protein extravasation, an exemplary functional assay of the neuronal mechanism of migraine. The results obtained for the panel of compounds in this model are summarized in Table I (infra).

Animal Model of Dural Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), were lowered through the holes in both hemispheres to a depth of 9 mm (rats) or 10.5 mm (guinea pigs) from dura.

The femoral vein was exposed and a dose of the test compound was injected intravenously (i.v.) at a dosing volume of 1 ml/Kg or, in the alternative, test compound was administered orally (p.o) via gavage at a volume of 2.0 ml/Kg. Approximately 7 minutes post i.v. injection, a 50 mg/Kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 mm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side, over the amount of extravasation in the unstimulated side, was calculated. Control animals dosed with only with saline, yielded a ratio of approximately 2.0 in rats and approximately 1.8 in guinea pigs. In contrast, a compound which effectively prevented the extravasation in the dura from the stimulated side would yield a ratio of approximately 1.0.

Dose-response curves were generated for each of the panel of compounds and the dose that inhibited the extravasation by 50% (ID$_{50}$) or 100% (ID$_{100}$) was approximated.

The respective $ID_{50}$ and/or $ID_{100}$ values, for each of the panel of compounds employed in the present invention, are summarized in Table I below.

TABLE I

| Inhibition of Dural Protein Extravasation (ng/Kg) | | | |
| --- | --- | --- | --- |
| Compound | Route of administration | $ID_{50}$ (ng/Kg) | $ID_{100}$ (ng/Kg) |
| I | i.v. | 6.5 (rat), 4.0 (Gpig) | — |
| II | i.v | 15 (rat) | — |
| III | i.v | .0053 (rat) | 0.10 |
| IV(b) | p.o | — | 0.01 |

What is claimed is:

1. A method of treating migraine comprising administering to a patient in need thereof an effective amount of a selective $iGluR_5$ receptor antagonist as given by the formula:

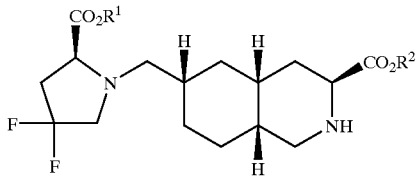

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, $C_1$–$C_6$ alkyl-morpholine or a pharmaceutically acceptable salt thereof.

2. A method of treating migraine comprising administering to a patient in need thereof a pharmaceutical composition comprising a selective $iGluR_5$ receptor antagonist as given by the formula:

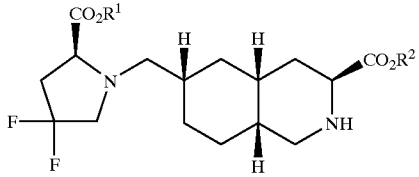

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, $C_1$–$C_6$ alkyl-morpholine, or a pharmaceutically acceptable salt thereof, in combination with one or more pharmaceutically acceptable carriers, diluents, or excipients.

3. A method of treating migraine comprising administering to a patient in need thereof an effective amount of a selective $iGluR_5$ receptor antagonist which is 3S, 4aR, 6S, 8aR-6-(((4-carboxy) phenyl) methyl)-1, 2, 3, 4, 4a, 5, 6, 7, 8, 8a-decahydroisoquinoline-3-carboxylic acid.

4. The method according to claim 1 wherein the selective $iGluR_5$ receptor antagonist is selected from 3S, 4aR, 6S, 8aR Ethyl 6-(((2S)-2-(Ethoxycarbonyl)-4,4-difluoropyrrolidinyl)methyl)-1, 2, 3, 4, 4a, 5, 6, 7, 8, 8a-decahydroisoquinoline-3-carboxylate, or 3S, 4aR, 6S, 8aR 6-(((2S)-2-(Carboxylic acid)-4,4-difluoropyrrolidinyl) methyl)-1, 2, 3, 4 4a, 5, 6, 7, 8, 8a-decahydroisoquinoline-3-carboxylic Acid.

5. A method of treating dural protein extravasation comprising administering to a patient in need thereof an effective amount of a selective $iGluR_5$ receptor antagonist as given by the formula:

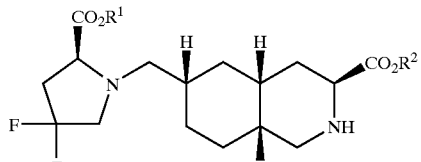

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, $C_1$–$C_6$ alkyl-morpholine or a pharmaceutically acceptable salt thereof.

6. A method of treating migraine comprising administering to a patient in need thereof an effective amount of a compound, or combination thereof, which possesses the activity of a selective $iGluR_5$ receptor antagonist as given by the formula:

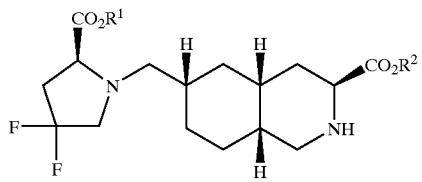

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, $C_1$–$C_6$ alkyl-morpholine or a pharmaceutically acceptable salt thereof.

7. A compound of the formula

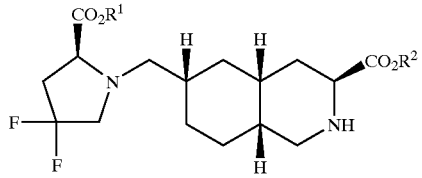

wherein $R^1$ and $R^2$ are each independently H, $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, $C_1$–$C_6$ alkyl-morpholine or a pharmaceutically accepatable salt thereof.

8. A compound according to claim 7 wherein $R^1$ and $R^2$ are each independently H or $C_1$–$C_{20}$ alkyl.

9. A compound which is 3S, 4aR, 6S, 8aR Ethyl 6-(((2S)-2-(Ethoxycarbonyl)-4,4-difluoropyrrolidinyl)methyl)-1, 2, 3, 4, 4a, 5, 6, 7, 8, 8a-decahydroisoquinoline-3-carboxylate, or a pharmaceutically acceptable salt thereof.

10. A compound which is 3S, 4aR, 6S, 8aR 6-(((2S)-2-(Carboxylic acid)-4,4-difluoropyrrolidinyl)methyl)-1, 2, 3, 4, 4a, 5, 6, 7, 8, 8a-decahydroisoquinoline-3-carboxylic acid, or a pharmaceutically acceptable salt thereof.

11. A compound which is 3S, 4aR, 6S, 8aR Ethyl 6-(((2S)-2-(Ethoxycarbonyl)-4,4-difluoropyrrolidinyl)methyl)-1, 2, 3, 4, 4a, 5, 6, 7, 8, 8a-decahydroisoquinoline-3-carboxylate.mandelate.

12. A pharmaceutical composition, which comprises a compound according to claim 7 in combination with one or more pharmaceutically acceptable carrier, diluents, or excipients.

13. A pharmaceutical composition, which comprises a compound according to claim 8 in combination with one or more pharmaceutically acceptable carrier, diluents, or excipients.

14. A pharmaceutical composition which comprises a compound which is 3S, 4aR, 6S, 8aR Ethyl 6-(((2S)-2-(Ethoxycarbonyl)-4,4-difluoropyrrolidinyl)methyl)-1, 2, 3, 4, 4a, 5, 6, 7, 8, 8a-decahydroisoquinoline-3-carboxylate, or a pharmaceutically acceptable salt thereof, in combination with one or more pharmaceutically acceptable carriers, diluents, or excipients.

15. A pharmaceutical composition which comprises a compound which is 3S, 4aR, 6S, 8aR 6-(((2S)-2-(Carboxylic acid)-4,4-difluoropyrrolidinyl)methyl)-1, 2, 3, 4, 4a, 5 6, 7, 8, 8a-decahydroisoquinoline-3-carboxylic acid, or a pharmaceutically acceptable salt thereof, in combination with one or more pharmaceutically acceptable carriers, diluents, or excipients.

16. A pharmaceutical composition which comprises a compound which is 3S, 4aR, 6S, 8aR Ethyl 6-(((2S)-2-(Ethoxycarbonyl)-4,4-difluoropyrrolidinyl)methyl)- 1, 2, 3, 4, 4a, 5, 6, 7, 8, 8a-decahydroisoquinoline-3-carboxylate.mandelate, in combination with one or more pharmaceutically acceptable carriers, diluents, or excipients.

\* \* \* \* \*